United States Patent [19]

Rowe, Jr. et al.

[11] Patent Number: 4,542,539
[45] Date of Patent: Sep. 24, 1985

[54] SURGICAL IMPLANT HAVING A GRADED POROUS COATING

[75] Inventors: Russell H. Rowe, Jr., Warrenton, Va.; Paul J. Lare, Bowie, Md.; Henry Hahn, Fairfax, Va.

[73] Assignee: Artech Corp., Falls Church, Va.

[21] Appl. No.: 575,624

[22] Filed: Jan. 31, 1984

Related U.S. Application Data

[63] Continuation-in-part of Ser. No. 357,744, Mar. 12, 1982, abandoned.

[51] Int. Cl.$^4$ .......................... A61F 1/00; A61F 5/04
[52] U.S. Cl. .......................... 623/16; 623/10; 623/11; 128/92 C; 128/92 G
[58] Field of Search .......................... 3/1.9, 1.91, 1.912, 3/1.911; 128/92 C, 92 CA, 92 G

[56] References Cited

U.S. PATENT DOCUMENTS

| | | | |
|---|---|---|---|
| 3,605,123 | 9/1971 | Hahn | 3/1.9 |
| 3,855,638 | 12/1974 | Pilliar | 3/1.9 |
| 4,206,516 | 6/1980 | Pilliar | 3/1.9 |
| 4,351,069 | 9/1982 | Ballintyn et al. | 3/1.9 |

OTHER PUBLICATIONS

Thesis submitted in partial fulfillment of the requirements for the degree of Master of Science (Engineering) at the University of Wisconsin by John T. Reynolds and entitled "Powder Metallurgy Fabrication of Cobalt—Base Alloy Surgical Implants", pp. 50 through 52, 1968.

Primary Examiner—Richard J. Apley
Assistant Examiner—David Isabella
Attorney, Agent, or Firm—Robert G. Crooks

[57] ABSTRACT

This biologically compatible surgical prosthetic implant has a multi-layer coating formed from metallic particles having sizes which increase in the direction from the metallic body of the implant toward the surface of the coating which is to interface with bone. The gradation is achieved by first depositing a layer of small particles, for example microspheres, of metallic coating material on the surface of the implant, then depositing progressively larger particles in subsequent layers. The particles may be deposited by any one of a number of well-known processes including but not limited to a flame-plasma process, in which several parameters are controlled as functions of the size of the particles.

The resultant coating has minimum density and maximum porosity at its outer surface to encourage ingrowth of bone. The density of the coating is maximized at the interface between the coating and the body of the implant, thereby substantially matching the mechanical and thermal properties of the body of the implant and the coating and achieving optimum adherence of the coating to the body of the implant.

17 Claims, 4 Drawing Figures

SURGICAL IMPLANT HAVING A GRADED POROUS COATING

BACKGROUND OF THE INVENTION

This Application is a continuation-in-part of application Ser. No. 06/357,744, filed by the same inventors on Mar. 12, 1982 now abandoned and entitled "GRADED POROUS COATINGS FOR SURGICAL IMPLANTS".

Our invention relates to surgical prosthetic implants, especially to implants having biologically compatible coatings formed from metallic particles characterized by a gradient of particle size.

For several years it has been known that the ingrowth of bone tissue into a surgical prosthetic implant can be facilitated if, prior to implantation, a porous coating is applied to all or part of the surface of the implant which is to be in contact with bone after implantation.

U.S. Pat. No. 3,605,123, issued on Sept. 20, 1971 to Henry Hahn, discloses a surgical implant or prosthetic device of high structural strength having a thin porous coating thereon to promote integration between the prosthetic device and the bone tissue in which it is implanted. The body of the implant is metallic in composition, and the coating is a porous layer of the same metallic material. However, the aforementioned Hahn patent does not disclose either a particulate coating comprising multiple layers each of different particle size or a coating applied in multiple layers characterized by particle sizes which increase in the direction away from the body of the implant.

U.S. Pat. Nos. 3,855,638 and 4,206,516, both issued to Robert M. Pilliar on Dec. 24, 1974 and June 10, 1980 respectively, disclose coated prosthetic devices. The '638 patent discloses a coating which has uniformly-sized and distributed pores between the metal particles of a single specified size range in the coating. The '516 patent also discloses a coated implant in which the porosity of the coating is substantially uniformly distributed. Pores of different sizes may be present, but only on *different parts of the surface* of the implant rather than in superposed, successively applied layers as in the present invention. Neither Pilliar patent discloses a multiple-layer coating of metallic particles in which the size of the particles increases in the direction away from the surface of the substrate.

U.S. Pat. No. 4,351,069, issued on Sept. 28, 1982 to Nicolaas Ballintyn et al, discloses a prosthetic device having a sintered thermoplastic coating with a porosity gradient. Ballintyn et al stated that metallic coatings are physiologically *unsuitable* for use on prosthetic devices and limited their invention to implants having *thermoplastic* coatings. The present inventors, on the contrary, have found that porous coatings of metallic particles on an implant formed from the same metal as the particles are *well suited* for use in human beings and, in addition, provide strength and other mechanical properties which cannot be achieved by thermoplastic materials.

In 1968, a thesis submitted to the University of Wisconsin by John T. Reynolds suggested porous surgical implants having a surface amenable to the ingrowth of tissue. However, Reynolds made no disclosure of a multi-layer metallic coating on a metallic implant in which the particles in the respective layers of the coating have sizes increasing in the direction away from the implant. Reynolds favored implants fabricated by powder metallurgy. The present inventors, on the other hand, have found that the strength of the implant is maximized if it is formed from coated solid metal, preferably titanium, although an alloy such as chromium-cobalt, or stainless steel, may also be used for this purpose.

SUMMARY OF THE INVENTION

It is an object of our invention to provide a surgical prosthetic implant biologically compatible with the human body, characterized by high structural strength, and having a porous multi-layer coating capable of promoting ingrowth of bone.

Another object of our invention is to provide a surgical prosthetic implant having a porous coating the outer surface of which substantially matches certain mechanical properties of bone, such as strength and modulus of elasticity.

A further object of our invention is to provide a coated surgical prosthetic implant in which the density of the porous coating adjacent the solid body of the implant nearly matches the body of the implant in certain mechanical properties, whereby any tendency of the coating to separate from the body of the implant is minimized.

These and other objects of our invention have been fulfilled by providing a surgical implant comprising a solid metal substrate and a porous coating comprising metallic particles of non-uniform size wherein a layer of the smallest-size particles is first deposited on the surface of the substrate as densely as possible, and layers of successively larger metallic particles are thereafter deposited in sequence. The resultant coating has maximum density at the interface between the coating and the substrate of the implant. The pores or spaces between the comparatively large particles of the outer layer are much greater than the minute pores between the small particles of the first layer. The size of the particles of the outer layer is chosen in such a way that the spaces therebetween are optimum for the promotion of bone ingrowth. The flame-plasma process is the preferred method for applying the metallic particles of all layers of the coating.

Our invention will be described in detail in the following specification, to be read in conjunction with the accompanying drawings, wherein.

Figure 2:
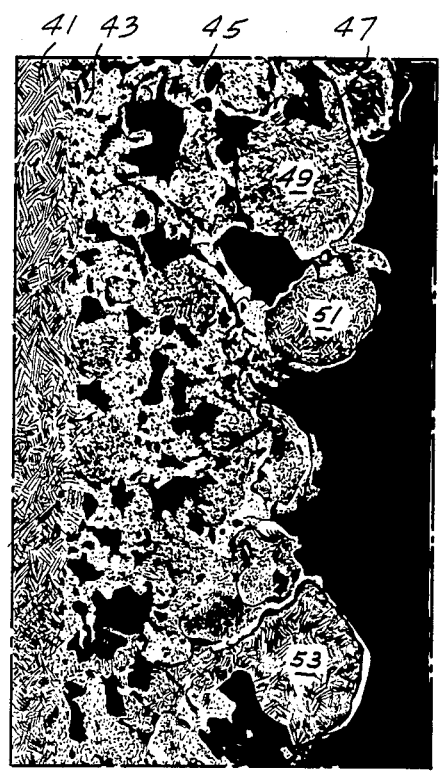
FIG. 2 is a cross-sectional view of an actual coated substrate as depicted in a micrograph taken by means of an optical metallograph focused on the plane surface of a specimen that has been sectioned and polished.
Figure 3:
Figure 4:
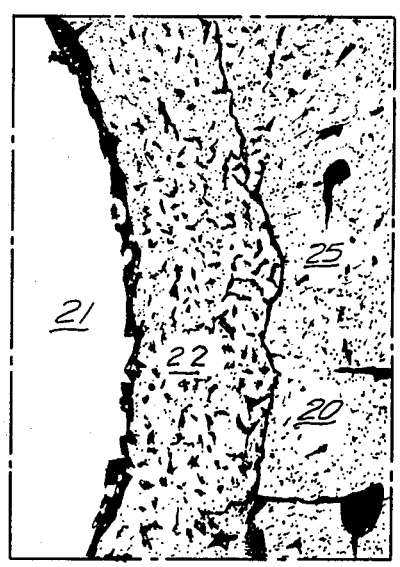

FIG. 3 is a scanning electron micrograph of the outer surface of a surgical implant that has been coated in accordance with our invention, depicting the porous structure into which bone ingrowth is to take place; and FIG. 4 is identical to FIG. 2 of the drawings of U.S. Pat. No. 3,605,123—Hahn and represents a bone implant having a coating of a single layer, showing some bone growth into that layer. FIG. 4 is thus one example of the prior art.

GENERAL DESCRIPTION OF THE INVENTION

The surgical implant according to our invention may serve to replace a diseased or damaged joint in the human body such as a hip, knee, or elbow. Alternatively, the implant in accordance with our invention may be employed in dental applications wherein the implant serves to affix bridgework to the lower jaw bone, or mandible, When an entire knee joint is replaced by an implant, the replacement is referred to as a "total knee system". When the upper portion of the human femur is utilized to support the stem portion of a hip prosthesis, the stem is fixed within the medullary space in the femur. A spherical ball affixed to the stem cooperates with a so-called "acetabular cup" which is fitted into a hemispherical recess in the pelvic bone. The construction in accordance with our invention is useful, for instance, in causing the pelvic bone to grow into the porous outer surface of the acetabular cup. An electron micrograph of the outer surface of such a cup appears in FIG. 3 of the drawings. The surface of the acetabular cup has openings of a size range chosen to encourage bone ingrowth thereinto. The size range of the openings is disclosed later in this specification.

The material for the implant in accordance with our invention may be chosen from a group of metals such as titanium or alloys which include an alloy of chromium and cobalt, an alloy of chromium, cobalt and molybdenum, and an alloy of titanium with aluminum and vanadium. We prefer to use the titanium alloy which consists of 90% by weight of titanium, 6% by weight of aluminum and 4% by weight of vanadium. This alloy is referred to in the industry as Ti-6Al-4V (ELI grade). The alloy displays a very high degree of strength, low brittleness and is biocompatible with the tissues and fluids of the human body. The modulus of elasticity of Ti-6Al-4V can be approximated to that of bone by coating the body of the implant with Ti-6Al-4V in sintered-powder, or in porous-body form. At one time, stainless steel was widely used as a material for surgical implants. However, we prefer to employ the aforementioned alloy of titanium. By virtue of its strength, elasticity, and lack of brittleness, it is far superior to other materials such as ceramics and plastics.

The bone implant in accordance with U.S. Pat. No. 3,605,123 is illustrated in FIG. 4 of our drawings, which is identical to FIG. 2 of the aforementioned prior-art patent. In that figure, the solid metal substrate of the bone implant 21 appears at the left of the figure. Upon the surface of the substrate is applied a porous coating 22. At the right-hand side of the figure is depicted the bone 20 which is shown to have grown into the irregular surface of coating 22. The '123 patent does not disclose a multiple-layer coating in which there is a gradient of particle size as in the present invention.

A particle size gradient in accordance with the principles of this invention is obtained preferably by using a coating comprising three successively applied layers of particles. However, more than three layers may be used, depending upon the requirements of a particular application, at the expense of additional labor and material. Whatever number of layers, greater than one, is selected, these layers match as nearly as possible the properties of the innermost layer to those of the metallic implant per se, and at the same time match as nearly as possible the properties of the outer surface of the outer layer of the coating to those of bone.

Figure 1:
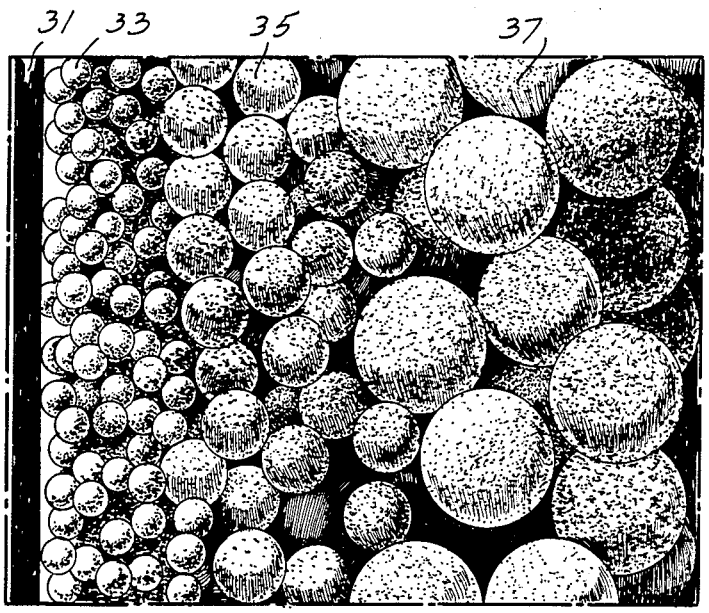
FIG. 1 is an idealized model of the substrate and coating of our invention, illustrating the gradient in size of the particles of three layers of the coating.

A schematic representation of our invention appears in FIG. 1 of the drawings. In that figure, substrate 31 of the bone implant appears at the left of the figure, while a layer of comparatively small particles 33 is applied thereto in a very dense array. An intermediate layer 35 of somewhat larger particles is in turn applied over layer 33, and an outer layer 37 of very large particles is in turn applied over layer 35. FIG. 1 is an idealized model which is presented to illustrate the principles of our invention, and this invention is not limited to layers of spherical particles. Even where the starting material for the layers comprises particles of material which are generally spherical in shape, the shape may depart somewhat from spherical even prior to application of the particles. *After* application of the particles, the shape thereof will have been very much distorted. In fact, we have found that with a starting material of generally spherical particles, the particles of the inner layer 33, after application to the body of the implant, will have been fused together in such a way that they will have lost their spherical shape. On the other hand, the particles of outer layer 37, because of their large size and the method of application thereof, will have retained somewhat more of their generally spherical configuration This distribution of particle size and shape is illustrated in FIG. 2 of the drawings, which is a cross-sectional view of a portion of an implant that has been sectioned and polished and photographed by means of a metallograph. Obviously, as with FIGS. 1 and 3 of the drawings, the size has been greatly magnified for the sake of clarity.

In FIG. 2, the substrate of the implant 41 appears at the left and carries thereon a very thin inner layer of small particles 43 which have been applied to the substrate and fused thereto as well as to one another. To the right of the inner layer 43 is a much thicker intermediate layer 45 which has been formed from larger particles that likewise have become distorted although not fused together to the same extent as inner layer 43. Finally, outer layer 47 is formed from still larger particles, three of which appear at 49, 51 and 53 and are recognizable as having been derived from particles that were originally generally spherical in shape. The reason for this particle retention of shape will be explained later in the specification. Although the implant of our invention is constructed by applying a plurality of distinct successive layers of particles, the process of application causes the individual layers to become less distinct from one another but still recognizable as distinct layers, as shown in FIG. 2.

In choosing material for the coating of our implant, we recognize that commercially available metallic powders have particle sizes which are not completely uniform. Each type of metallic powder includes a *range* of particle sizes. However, the range can be reduced by screening the powdered material as is well known in metallurgy. We prefer to screen the particles in such a way that the ranges of particle size in no two of the layers will overlap. In any event, the aggregation of particles which form the inner layer and which interface with the substrate of the implant will have the greatest density and the smallest degree of porosity. On the other hand, the aggregation of particles forming the outer layer of the coating, although they are the largest in size, will have the smallest density and the highest degree of porosity. Because particle size is a controllable factor, whereas porosity in the completed implant is not directly controllable, we prefer to speak in terms of particle size rather than porosity. Although there is certainly a relationship between particle size and porosity, the relationship between particle size and porosity is imprecise and non-linear. As will be explained hereafter, the method of application greatly influences the porosity, whereas the particle size can be explicitly stated prior to formation of the coating.

Clearly, the mean value of the size range of the particles in the second layer should be greater than the mean value of the size range of the particles in the first layer; the mean value of the size range of the particles in the third layer should be greater than the mean value of the size range of the particles in the second layer; and so on, if there are more than three layers in the coating.

By way of example, which may be regarded as typical but not limiting, we have found that fine particles of sizes within the range (−100+400) mesh are suitable for use in forming the inner layer. The thickness of this coating may be from about 0.001″ to about 0.005″. The microstructure of this layer, applied as will be explained hereinafter, exhibits little porosity and has physical properties which nearly match those of the substrate of the implant.

For a second layer of the coating, we have found that metallic particles in the range (−60+150) mesh are suitable. The thickness of the second layer may be from about 0.005″ to about 0.025″. When applied by the flame-plasma process, the pores between the particles in this layer will range in size from approximately 15 micrometers to about 50 micrometers. In view of the indistinctness of the boundaries between layers of the coating, all given values of layer thickness should be regarded as illustrative but not in any sense limiting. Likewise, the values of pore size should not be taken as limits because pore size varies within each layer and as a function of the method of application and the method of measurement.

In forming a third and outer layer of the coating, we prefer to use particles of approximately (−20+60) mesh and to build up a layer of thickness between about 0.006″ and 0.040″. The openings or pores between the particles of the outer layer will range in size up to approximately 500 micrometers A pore size range between 100 and 500 micrometers is such as to encourage bone ingrowth. In the outer 0.005″ of the outer layer of coating, the particles may be distributed so that their density is as low as ten percent of the maximum theoretical density and so that some pores may be as large as 600 micrometers in size.

Although the application of materials to a substrate by means of the flame-plasma process is well known, we shall present below a table illustrating typical spraying parameters, such as the feed rate of the metal particles, and the flow rate of the carrier gas. Also included in the table are suggested distances by which the spray gun should be spaced from the implant during the spraying process.

Perhaps the most interesting of the parameters included in the table is the angle of incidence of the sprayed particles upon the surface of the implant substrate. It is noteworthy that the particles of the innermost layer are sprayed directly against the surface of the substrate in a direction normal to that surface. In this way, the particles of the inner layer are packed as densely as possible on the surface of the substrate. On the other hand, the particles of the second or intermediate layer are applied at an angle of incidence of about 45°. Finally, the particles of the outer layer are applied at a grazing angle of 75° to 85° incidence. Thus, the larger particles of the outer layer are directed across the surface of the intermediate layer in such a way that the large particles of the outer layer will be arranged very irregularly, with varying amounts of space between them. This resultant irregularity is illustrated graphically in FIG. 2 of the drawings.

Before the coating is applied, it is desirable to clean the surface of the implant by grit blasting or some equivalent process. It is also possible to roughen slightly the metal surface of the implant, if desired.

| | Inner Layer | Intermediate Layer | Outer Layer |
| --- | --- | --- | --- |
| Coating Thickness, | | | |
| mm. | .013 | 0.38 | 1.04–1.17 |
| (in.) | (0.005) | (0.015) | (0.040–0.045) |
| Plasma Current, | | | |
| A (d-c) | 600 | 520 | 440 |
| $^b$ Gas Flow Rates, Std. ft$^3$/h. | | | |
| Total | He 90$^a$, H$_2$10 | He 90$^a$, H$_2$10 | N$_2$80, H$_2$ 20–25 |
| Carrier Gas (Feeder) | 3 | 8 | 18 |
| Feed Rate/g/s | 0.2 | 0.6 | 0.3 |
| Gun Distance, | | | |
| cm. | 10–15 | 20–25 | 10 |
| (in.) | (4–6) | (8–10) | (4) |
| Angle of Incidence | 0° | 45° | 75–85° |

$^a$ Flow rate indicated on gauge calibrated for N$_2$.
$^b$ One cubic foot per hour equals 7.86x10$^{-6}$ m$^3$/s.

In order to be successful, a surgical implant must have three important characteristics. They are as follows:

1. It must be biocompatible;
2. It must have high strength and moderate weight; and
3. It must match as nearly as possible the physical properties of the bone at the surface where bone ingrowth is to take place, thereby preventing "resorption" of the bone.

Fortunately, a bone implant made in accordance with our invention has all of the aforementioned characteristics. They will now be explained in more detail.

1. In order to be biocompatible, the bone implant must be made of a material that will not corrode in the body fluids and will not be rejected by the human body. By choosing to make both the implant and its coating of the same material, we ensure biocompatibility.

Since there can be no electrolytic action between the implant and its coating if they are formed of the same material, corrosion is precluded. Moreover, if, as we prefer, the material chosen for the implant and its coating is titanium or the alloy Ti-6Al-4V, rejection by the human body is also precluded because the titanium and and the alloy have proven to be metals which the human body can tolerate within it. If one chooses another alloy such as an alloy of cobalt and chromium, then the material employed in the coating of the implant should be the same alloy of cobalt and chromium. If desired, the coating of a titanium implant can be made of titanium sponge, which is less expensive than the aforementioned alloy of titanium. A still further possibility is to use the alloy in the first two layers of the coating, but to substitute the less expensive titanium sponge for the alloy in the outer layer of the coating, for which the most material is needed. Finally, one of the aforementioned titanium materials might be chosen for the inner and outer layers of the coating, while the other material is employed in the intermediate layer or layers. The source of titanium for the coating layers might alternatively be a powder of titanium hydride which is projected against the implant by a flame-plasma spray gun and which is reacted to predominantly titanium during the spraying process.

2. The implant in accordance with our invention satisfies the second criterion in that it is very strong and is not brittle. An implant replacing a joint, such as the hip, of a human body bears several kinds of load. At times, the load can exceed three times the weight of the body. Although some flexural and torsional stresses may be applied to the implant, the principal loads placed thereon in the human body are likely to be compressive and shear stresses. In a joint such as the hip, the shear stresses are the most important. The implant in accordance with our invention is particularly well adapted to handle shear stresses without failing at the outer surface of the coating layer. The openings in the metal of the coating encourage bone ingrowth, thereby producing a physical locking effect just as the roots of a tree interlock with the earth and stones under the tree. Not only does the bone interlock with the particles of the coating, but it also fills the voids and strengthens the outer layer of the coating. Without such bone ingrowth, the outer layer of the coating, being very porous, would not be strong. However, when the bone substantially fills the voids between the particles of the coating, the resultant structure becomes exceedingly strong. Thus, shear stresses can be satisfactorily transmitted between the implant and the host bone.

A second aspect of strength is the ability of the implant to transmit, without failing, shear stresses between the coating and the solid metal substrate of the implant. By first applying very small particles very densely packed on the surface of the substrate, we have been able to maximize the strength at the interface between the substrate and the coating. We thus avoid any tendency of the coating to separate from the substrate or to slide thereon. Laboratory tests which we have made show that the strength of the bond between the coating and the substrate is approximately 1,000 lbs. per square inch of surface. The shear strength which characterizes the present invention is dramatically higher than the corresponding shear strength which would characterize an implant having a plastic coating on a metal substrate. The high shear strengths which prevail at the interface between the inner layer of coating and the substrate in the present invention can be attributed to the deposition of molten particles on the surface of the substrate. This molten material covers a much higher proportion of the surface of the substrate than would be the case with particles of sintered plastic material, where only a comparatively small portion of the particles may be in actual contact with the substrate.

Another of the mechanical properties of our invention, the modulus of elasticity, also distinguishes it from the prior art. The modulus of elasticity of solid titanium alloy is about $17 \times 10^6$ psi. The modulus of elasticity of a *coating* formed from *particles* of titanium alloy can range from $1.5 \times 10^6$ psi up to nearly $17 \times 10^6$ psi, depending upon the particle size and the aggregate density thereof when applied to the surface of a solid metal implant. By choosing a titanium alloy powder having a size in the range of $(-100+400)$ mesh, we form an inner layer having a modulus of elasticity of about 15 or $16 \times 10^6$ psi, thereby nearly matching the modulus of the solid metal substrate. Thus, any tendency of the coating to separate from the substrate by reason of dissimilar "stretching" characteristics is minimized.

Similarly, the size of the particles chosen for the *outer* layer in the range $(-20+60)$ mesh leads to an outer layer having a modulus of elasticity of about $2.6 \times 10^6$ psi, which nearly matches the modulus of elasticity of the major human bones such as the femur and the tibia.

U.S. Pat. No. 4,351,069—Ballintyn et al recommends the use of certain thermoplastic materials in a coating for an implant. However, the modulus of elasticity of the thermoplastic materials recommended by Ballintyn et al ranges from about $0.25 \times 10^6$ psi to about $0.50 \times 10^6$ psi. These values of modulus are only a small fraction of the values of modulus of human bone. Thus, there would be a tendency in the prior-art implant for the shear stresses between the bone and the coated implant to cause failure at the interface between the coating and the bone. The present invention avoids the chance of such failure.

3. One of the characteristics of human bone is that, if not loaded, it will atrophy or "resorb". Accordingly, where certain portions of prior-art implants do not actually transmit load to the bone or receive load from the bone, the bone resorbs or withdraws from contact with the implant. As resorption continues, the inplant becomes loose and wobbly in the bone. This can take place even if the implant has been "cemented" to the bone with methyl methacrylate or other so-called bone cement. Resorption has frequently made it necessary for prior-art implants to be replaced, requiring surgical operations subsequent to the operation during which the implant was installed. Sometimes the repeated surgery causes further damage to the bone, thereby precluding a satisfactory implantation during the *second* operation.

An implant in accordance with our invention avoids resorption and the consequent loosening of the implant. By encouraging bone ingrowth into every pore of the outer layer of the coating and even the intermediate layer or layers of the coating, we achieve a structure in which forces are transmitted from every portion of the bone to every portion of the implant. Thus, the load is distributed in the bone, and there is no tendency for any particular part of the bone to resorb.

We have noted that the disclosure of the Ballintyn et al patent "teaches away" from the present invention by indicating that coatings of metallic particles are inherently *unsuitable* for use on prosthetic devices. Ballintyn et al instead recommended the use of a sintered thermoplastic coating. One of the advantages of our invention is that the metallic particles of the coating can be applied by a process such as flame-plasma spraying, which produces a strong bond among the particles themselves and with the substrate. Flame-plasma spraying is preferable to sintering because the latter lowers the fatigue strength of the substrate. In view of the repeated stresses that are applied to the substrate of an implant, any lessening of the fatigue strength thereof is undesirable and might lead to failure of the implant after a certain number of cyles of use. When particles are applied by the plasma spray process, the temperature of the substrate is not raised to a level that would cause deterioration of fatigue strength. The layered coating of our invention may be obtained by application processes other than flame spraying which do not seriously lessen fatigue strength.

Although our invention is defined by the appended process and article claims, it will be convenient to summarize the essential features of our invention both as to the implant and as to the process for manufacturing it:

1. The implant is formed from metal and has a coating of metallic particles;

2. The coating is applied to the implant in a *plurality* of layers; and

3. The particles of metallic powder comprising the coating are graded so that their size increases in a direction progressing away from the body of the implant toward the outermost layer, which contacts the bone and into which the bony ingrowth first takes place.

While our invention has been described in connection with specific embodiments thereof and in specific uses, various modifications thereof will occur to those skilled in the art without departing from the spirit and scope of the invention as set forth in the appended claims.

The terms and expressions which have been employed in this specification are used as terms of description and not of limitation, and there is no intention in the use of such terms and expressions to exclude any equivalents of the features shown and described or portions thereof, but it is recognized that various modifications are possible within the scope of the invention claimed.

We claim:

1. A posthetic implant comprising the combination of a metallic substrate and a coating on at least a portion thereof, in which such coating comprises first and second layers of metallic particles disposed with said first layer overlying and fused to said metallic substrate and said second layer overlying and fused to said first layer, wherein the sizes of said particles in said first layer are within the range ($-100+400$) mesh and wherein the sizes of said particles in said second layer are within the range ($-60+150$) mesh.

2. A prosthetic implant comprising the combination of a metallic substrate and a coating on at least a portion thereof, in which said coating comprises two layers of metallic particles disposed with the first such layer overlying and fused to the surface of said metallic substrate and forming the inner of said two layers, and with the second such layer overlying and fused to said first layer and being contiguous thereto and forming the outer of said two layers, the particles of said first layer having a first predetermined size within the range $-100+400$ mesh, the particles of said second layer having a second predetermined size within the range $-60+150$ mesh, and the mean value of said second predetermined size range being selected to be greater than the mean value of said first predetermined size range.

3. The implant of claim 2 wherein the particles of said coating are of the same material as the substrate, and said coating and substrate are both biologically compatible with human bone tissue.

4. The implant of claim 2 wherein the metal of said substrate is selected from the group comprising stainless steel, titanium alloys, elemental titanium, and chromium-cobalt alloys.

5. The implant of claim 2 wherein said second and outer layer has pore sizes ranging upward to about 500 micrometers near its outer surface.

6. The implant of claim 2 wherein said first layer has a thickness of about 0.001" to about 0.005", and said second layer has a thickness of about 0.005" to about 0.025".

7. A method of coating a selected portion of the surface of a metallic prosthetic implant substrate comprising the successive steps of:
(a) providing particulate metallic coating material in three predetermined size ranges, a first size range ($-100+400$) mesh, a second size range ($-60+150$) mesh, and a third size range ($-20+60$) mesh;
(b) applying to at least a portion of the surface of said implant substrate a first layer comprising said particulate metallic material having said first size range;
(c) applying to said first layer said particulate metallic coating material having said second size range to form a second layer overlying and bonded to said first layer and contiguous thereto; and
(d) applying to said second layer said particulate metallic coating material having said third size range to form a third layer overlying and bonded to said second layer and contiguous thereto.

8. The method of claim 7 wherein each of said steps (b), (c) and (d) of applying comprises depositing said particulate metallic coating material by means of a flame-plasma-spraying process.

9. The method of claim 8 wherein said step of depositing includes providing means for controlling process parameters so that the resultant density decreases and the pore size increases in coating layers successively applied to the surface of said implant.

10. The method of claim 9 wherein said step of depositing comprises grading the density and porosity of each layer so that the maximum density of each layer is in the region of the layer nearest the surface of said substrate and so that the maximum porosity of each layer is in the region of such layer most remote from the surface of said substrate.

11. A prosthetic implant comprising the combination of a metallic substrate and a coating on at least a portion thereof, in which said coating comprises three layers of metallic particles disposed with the first such layer overlying and fused to the surface of said metallic substrate and forming the innermost of said three layers, the second such layer overlying and fused to said first layer and being contiguous thereto, and the third such layer overlying and fused to said second such layer and being contiguous thereto and forming the outermost of said three layers, in which the sizes of said particles of said first layer are within the range ($-100+400$) mesh, the sizes of said particles of said second layer are within the range($-60+150$) mesh and the sizes of said particles of said third layer are within the range ($-20+60$) mesh.

12. The implant of claim 11 wherein said coating is graded in density and porosity with said third and outermost layer being the most porous.

13. The implant of claim 11 wherein the particles of said coating are of the same material as the substrate, and said coating and substrate are both biologically compatible with human bone tissue.

14. The implant of claim 11 wherein the metal of said substrate and said coating is selected from the group comprising stainless steel, titanium alloys, elemental titanium, and chromium-cobalt alloys.

15. The implant of claim 11 wherein said first and third layers are formed from substantially identical metals.

16. The implant of claim 11 wherein said third and outermost layer has pore sizes ranging upward to about 500 micrometers near its outer surface.

17. The implant of claim 11 wherein said first layer has a thickness of about 0.001" to about 0.005", said second layer has a thickness of about 0.005" to about 0.025", and said third layer has a thickness of about 0.006" to about 0.040".

* * * * *